United States Patent
Jackson et al.

(10) Patent No.: US 6,527,717 B1
(45) Date of Patent: Mar. 4, 2003

(54) TISSUE MOTION ANALYSIS MEDICAL DIAGNOSTIC ULTRASOUND SYSTEM AND METHOD

(75) Inventors: John I. Jackson, Menlo Park, CA (US); Randall L. Schlesinger, San Mateo, CA (US); John W. Allison, Los Altos, CA (US)

(73) Assignee: Acuson Corporation, Mountain View, CA (US)

( * ) Notice: Subject to any disclaimer, the term of this patent is extended or adjusted under 35 U.S.C. 154(b) by 126 days.

(21) Appl. No.: 09/608,235

(22) Filed: Jun. 30, 2000

Related U.S. Application Data
(60) Provisional application No. 60/188,515, filed on Mar. 10, 2000.

(51) Int. Cl.[7] .................................................. A61B 8/00
(52) U.S. Cl. ........................ 600/437; 600/443; 600/441; 128/916
(58) Field of Search ................................ 600/437, 441, 600/438; 348/443; 382/128; 128/916

(56) References Cited

U.S. PATENT DOCUMENTS

| | | | |
|---|---|---|---|
| 5,353,354 A | * 10/1994 | Keller et al. | ................ 382/128 |
| 5,415,175 A | 5/1995 | Hanafy et al. | |
| 5,785,655 A | * 7/1998 | Goodsell et al. | ............ 600/441 |
| 5,876,345 A | 3/1999 | Eaton et al. | |
| 5,899,861 A | * 5/1999 | Friemel et al. | ............. 128/916 |
| 6,014,473 A | 1/2000 | Hossack et al. | |
| 6,099,471 A | * 8/2000 | Torp et al. | ................... 600/438 |
| 6,222,948 B1 | * 4/2001 | Hossack et al. | ............ 348/443 |

* cited by examiner

Primary Examiner—Marvin M. Lateef
Assistant Examiner—Ruby Jain

(57) ABSTRACT

Accurate tissue motion systems and methods are provided. Motion of the ultrasound transducer is accounted for in estimates at tissue motion. Correcting for transducer motion better isolates localized tissue contractions or expansions, such as motion of the myocardial muscle or fibers. Accurate motion estimation is also provided by determining an angle of motion from the ultrasound data. The angle of motion is used to adjust velocity estimates, providing two-dimensional velocity vectors (i.e. motion estimates comprising motion in at least two dimensions). Movement of tissue is determined by correlating speckle or a feature represented by two different sets of ultrasound data obtained at different times. Additional aspects include tracking the location of a tissue of interest. A characteristic of strain, such as the strain rate or strain, is calculated for the tracked tissue of interest. Ultrasound data associated with different positions relative to the transducer are selected as a function of the tracking and used to determine the characteristic of strain. Motion estimates corrected for transducer motion may also be used to determine a strain or strain rate. In yet another aspect, motion estimates are generated with data from an intra-cardiac transducer array. The characteristic of strain is determined from the motion estimates. Other aspects discussed above may be used with an intra-cardiac transducer array, providing accurate motion analysis based on imaging from within the heart.

22 Claims, 3 Drawing Sheets

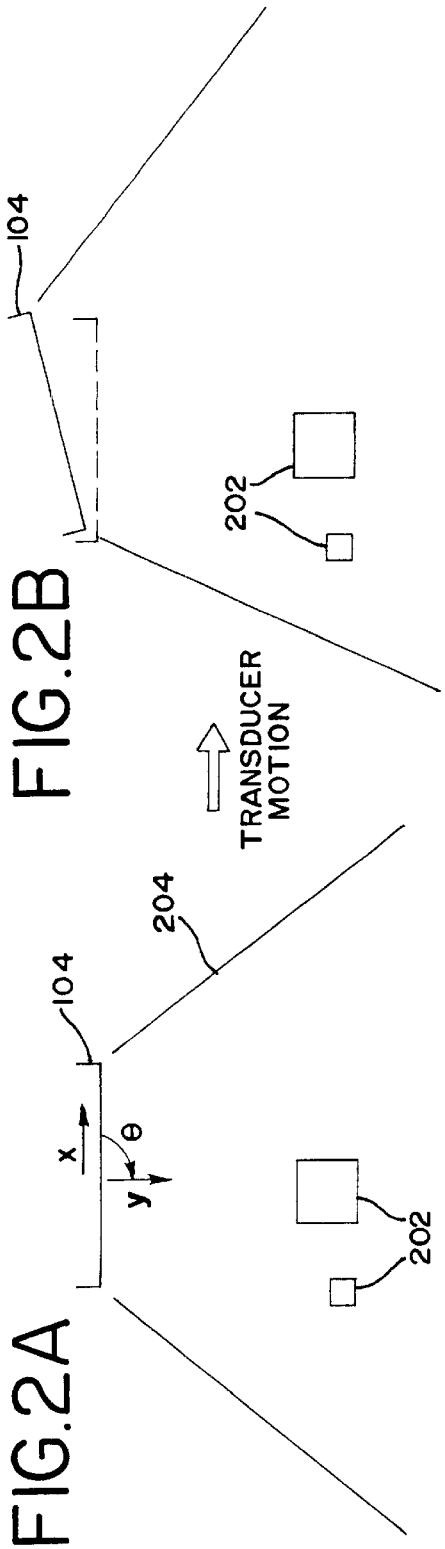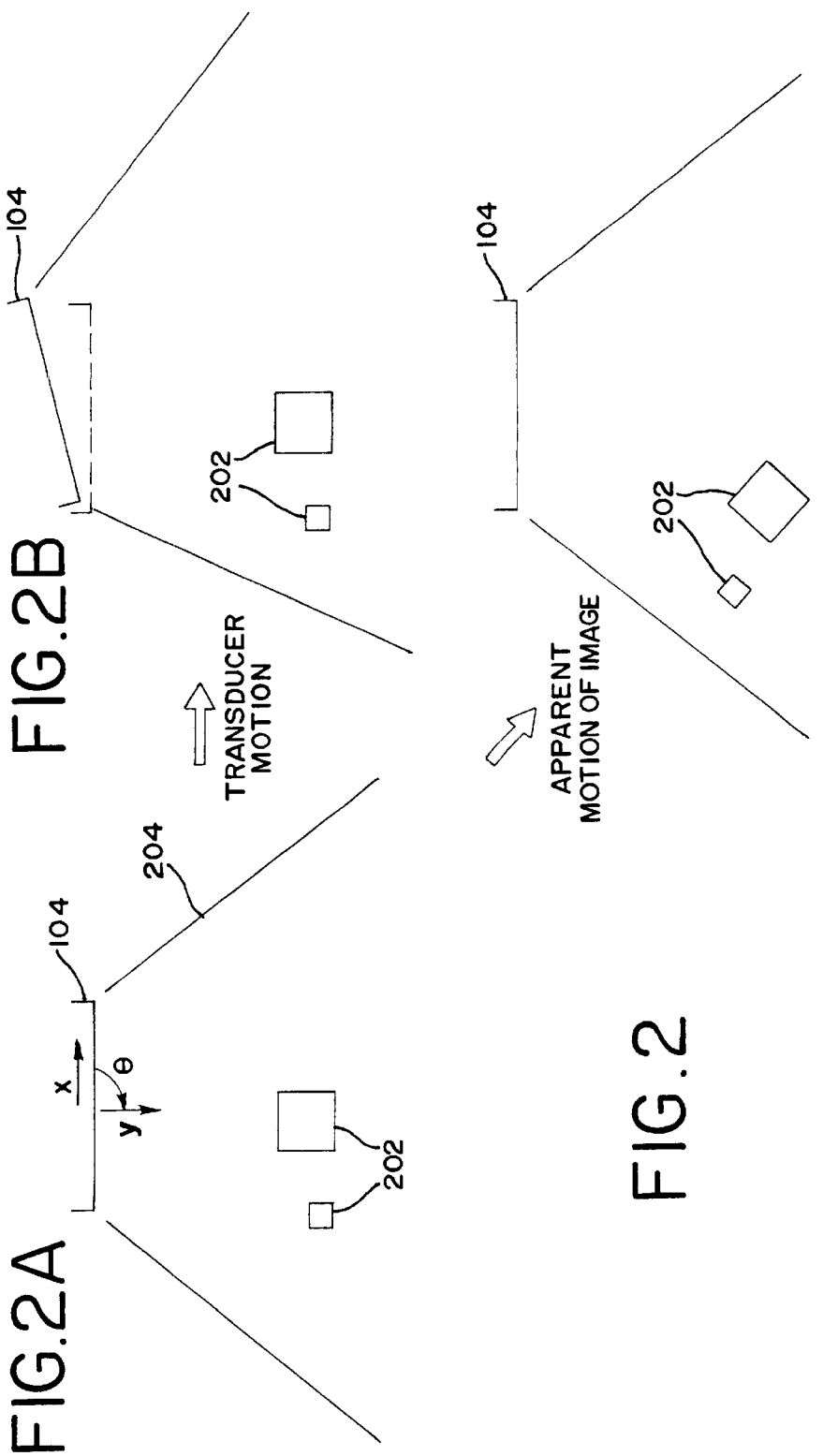

TISSUE MOTION ANALYSIS MEDICAL DIAGNOSTIC ULTRASOUND SYSTEM AND METHOD

RELATED APPLICATIONS

This application is a continuation-in-part of and claims the benefit of the filing date pursuant to 35 U.S.C. §119(e) of Provisional Application Ser. No. 60/188,515, filed Mar. 10, 2000, for a MEDICAL DIAGNOSTIC ULTRASOUND SYSTEM AND METHOD FOR TISSUE MOTION ANALYSIS, the disclosure of which is hereby incorporated by reference.

BACKGROUND

This invention relates to a medical diagnostic ultrasound system and method for tissue motion analysis. In particular, techniques for improving estimates of motion from ultrasound data and characterizing the motion are provided.

Medical diagnostic ultrasound systems operate in various modes. Doppler tissue imaging mode is used to assist in diagnosis of heart tissue or other moving tissue structures. The ultrasound data is filtered with a clutter filter or other device to isolate information associated with tissue. The velocity of the tissue information is determined. The energy or variance of the tissue information may also be determined.

The velocities estimated from the ultrasound data represent velocities along one dimension. The velocities are estimated along an associated scan line, so may not represent the true magnitude of the velocity of the target tissue. To obtain more accurate representations of the actual velocity of the target, angle corrections are performed. In one system, the angle between the direction of movement of the target and the ultrasound beam is assumed to be towards a common point or location set by the user.

Other embodiments operate on velocities representing fluid flow. The user indicates a direction of flow of fluids, and the velocity of the fluids is determined as a function of the magnitude of velocity along each ultrasound line and the user input angle. For example, U.S. Pat. No. 5,785,655 discloses angle correction for velocity data along a line of study.

Tissue Doppler velocity information is used to compute the velocity gradient or strain rate. For example, a user inputs a series of connected line segments in a two-dimensional image. The ultrasound system calculates the strain rate as a function of velocities along those line segments.

The strain of tissue has been calculated from the strain rate. A time integral of the strain rate is typically started at an R-wave of a heart cycle and graphed through the cardiac cycle. Generally, only one component of the strain rate, such as a component along one direction, is integrated. Based on the assumption that all motion is in that one direction, the peak of the strain indicates the peak contraction of a piece of tissue. For healthy myocardial fibers at rest, the peak strain is typically around 16 percent, where the strain is multiplied by 100 and described as a percentage.

BRIEF SUMMARY

The present invention is defined by the following claims, and nothing in this section should be taken as a limitation on those claims. By way of introduction, the preferred embodiments described below include methods and systems for accurate analysis of tissue motion based on ultrasound data. Motion of the ultrasound transducer is accounted for in estimates of tissue motion. Correcting for transducer motion better isolates localized tissue contractions or expansions, such as motion of the myocardial muscle or fibers. Accurate motion estimation is also provided by determining an angle of motion from the ultrasound data. The angle of motion is used to adjust velocity estimates, providing two-dimensional velocity vectors (i.e. motion estimates comprising motion in at least two dimensions). Movement of tissue is determined by correlating speckle or a feature represented by two different sets of ultrasound data obtained at different times. Decorrelation may be used to determine elevational motion.

Additional aspects include tracking the location of a tissue of interest. A characteristic of strain, such as the strain rate or strain, is calculated for the tracked tissue of interest. Ultrasound data associated with different positions relative to the transducer are selected as a function of the tracking and used to determine the characteristic of strain. Motion estimates corrected for transducer motion may also be used to determine a strain or strain rate.

In yet another aspect, motion estimates are generated with data from an intra-cardiac transducer array. The characteristic of strain is determined from the motion estimates. Other aspects discussed above may be used with an intra-cardiac transducer array, providing accurate motion analysis based on imaging from within the heart.

Further aspects and advantages of the invention are described below in conjunction with the preferred embodiments.

BRIEF DESCRIPTION OF SEVERAL VIEWS OF THE DRAWINGS

FIGS. 2A–2C are graphical representations showing the effect of relative movement between a transducer and a tissue of interest.

DETAILED DESCRIPTION OF THE PREFERRED EMBODIMENTS

Accurate analysis of tissue motion is provided by (1) correction for transducer motion contribution to motion estimates, (2) determination of two-dimensional motion vector estimates using motion tracking and Doppler information, and (3) using these inproved estimates to determine a characteristic of strain, such as strain or strain rate. Tracking of tissue movement also allows for a characteristic of strain to be determined for a particular moving tissue, rather than measuring strain at a point set relative to the transducer. Where tissues are moving in different directions within a scanned region, a plurality of local determinations of two-dimensional motion vectors provides accurate estimates of motion throughout a scan region. These methods provide for accurate strain or strain rate calculations using intra cardiac ultrasound transducers. For example, estimates of motion are corrected to account for the movement of the intra-cardiac transducer.

Figure 1:
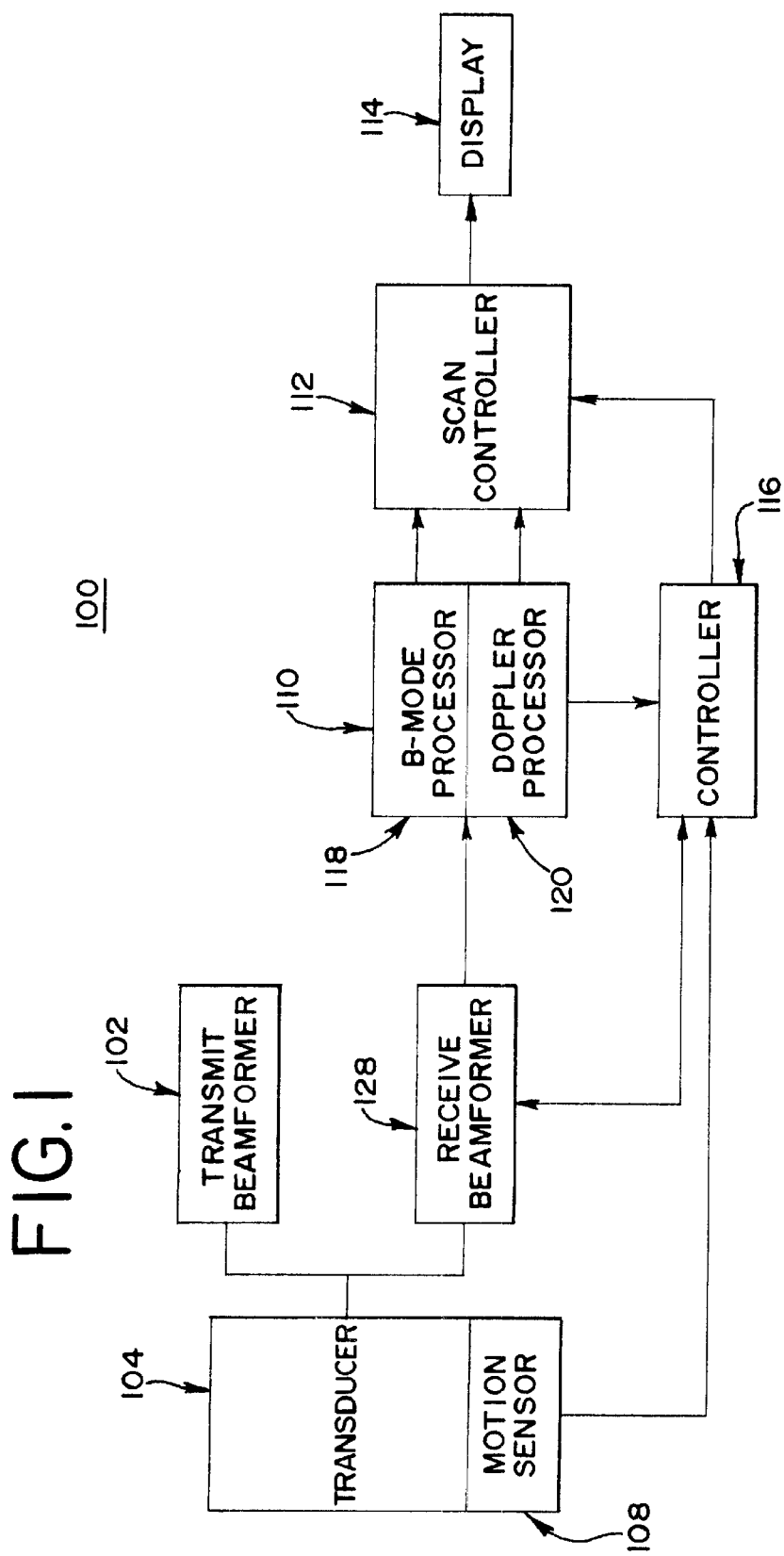
FIG. 1 is a block diagram of one embodiment of a medical diagnostic ultrasound system for tissue motion analysis.

FIG. 1 shows one embodiment of a medical diagnostic ultrasound system for tissue motion analysis 100. The system 100 comprises an ultrasound system, such as one of the 128XP®, Aspen™ or Sequoia® ultrasound systems. Ultrasound systems from other manufacturers may be used. Alternately, the ultrasound system 100 comprises a remote workstation, such as a processor or other device for displaying an ultrasound image from a scan of a patient at a remote location. For example, an Aegis® Workstation from Acuson Corporation is used.

The system 100 of the embodiment shown in FIG. 1 includes a transmit beamformer 102, a transducer 104, a motion sensor 106, a receive beamformer 108, a motion processor 110, a scan converter 112, a display 114 and a controller or strain processor 116. Fewer or additional components may be included, such as including a three-dimensional processor or using only a processor architecture with a mechanism to receive ultrasound data and generate a display.

The transducer 104 comprises at least one piezoelectric element. For example, the transducer 104 comprises a phased array of a plurality of elements. The elements are arranged in linear, curvilinear, annular, sector or other array format. Two-dimensional or 1.5 dimensional arrays may also be used. The transducer 104 is adapted for use external to the body, such as including a hand-held casing. Alternatively, the transducer 104 is adapted for use within the target's body, such as an endocavity transducer. As another example, the transducer 104 is mounted on a catheter. Intra-cardiac transducers include radial arrays or linear arrays. Other array formats may be used. The catheter mounted transducer 104 is inserted within the cardiac system of the target. Intra-cardiac transducers are disclosed in U.S. Pat. Nos. 5,876,345, and 5,415,175, the disclosures of which are incorporated herein by reference. As yet another example, the transducer 104 comprises a transducer as provided on the catheter sold by Acuson Corporation as the Acu NAV transducer. Other transducers may be used, such as transducers adapted for different scanning formats.

The motion sensor 106 comprises a position sensor for determining a location of the transducer 104 relative to the target or other reference points. In one embodiment, the motion sensor 106 comprises a magnetic or electromagnetic position sensor, such as the electromagnetic positioners manufactured by Biosense of New York or Ascension Technology of Burlington, Vt. Orthogonal coils are placed on the transducer 104 and in a nearby transmitter. By sequencing transmissions through the transmitter coils and measuring signals on each of the sensor coils, the location and orientation of the sensor coil is determined. Based on the position and orientation of the patient relative to the transmitter coils, the location and orientation of the transducer 104 is determined. Movement of the transducer 104 is calculated as a function of the position determined at two different times. In alternative embodiments, ultrasound data or other sources of information are used to determine the position or movement of the transducer 104 as discussed below. The position or motion information is provided from the motion sensor 106 to the controller 116.

The transmit beamformer 102 and receive beamformer 108 comprise analog or digital components for acoustically scanning a region of a target using the transducer 104. Acoustical energy is generated by the transducer 104 in response to transmit waveforms from the transmit beamformer 102. The transducer 104 receives responsive acoustic energy reflected from tissue and fluid structures within the target. The receive beamformer 108 obtains electrical signals from the transducer 104 and applies appropriate delays. The delayed information is summed to generate ultrasound data representing tissue and fluid structures along each receive beam of acoustic energy.

The motion processor 110 comprises a B-mode processor 118 and a Doppler processor 120 for processing the receive beamformed ultrasound data (e.g. radio frequency or in-phase and quadrature data). In alternative embodiments, the controller 116 or another processor performs motion processing as discussed below based on data from the receive beamformer 106 or from either of the B-mode processor 118 or Doppler processor 120.

The Doppler processor 120 comprises a digital signal processor, general processor, ASIC or other analog or digital devices for estimating velocity, energy and/or variance for one or more spatial locations along each scanline. Autocorrelation or time shift processing may be used.

The Doppler processor 120 optionally includes a clutter filter. The clutter filter comprises a digital signal processor, general processor, ASIC or other device performing high pass, low pass or band pass filtering to isolate information associated with tissue movement from information associated with fluid flow. Alternatively, thresholding is used to distinguish tissue movement from fluid flow. The Doppler processor 120 outputs tissue velocity magnitudes.

The B-mode processor 118 comprises a digital signal processor, processor, ASIC or other device for determining the envelope, amplitude, intensity, or power of the received ultrasound data. B-mode ultrasound data typically includes more speckle information and tissue feature information than Doppler ultrasound data. As discussed below, B-mode ultrasound data is preferably used for tracking an angle of motion and/or determining motion magnitude from speckle or feature information. Alternatively, Doppler ultrasound data is used.

The ultrasound data from the motion processor 110 is provided to the scan converter 112. The scan converter formats the ultrasound data into a Cartesian coordinate format for display on the display 114.

The motion processor 110 may output motion estimates or other motion related information to the controller 116. The controller or strain processor 116 comprises a digital signal procesor, general processor, ASIC or combination thereof for calculating characteristics of strain and controlling operation of the system 100. In alternative embodiments, the strain processor comprises a dedicated processor separate from the controller 116. The controller or strain processor 116 also performs correlational analysis as discussed below for tracking or determining an angle of motion, and/or estimating a velocity vector. Alternatively, the motion processor 110 performs these calculations. The processors and associated memories used for calculating strain or strain rate, estimating motion, determining transducer motion and/or tracking tissue or speckle may comprise one or more processors within any of the various subsystems of the ultrasound system 100, within a workstation or within a personal computer. In one embodiment, a separate computer external to or within the ultrasound system is used for performing correlation or tracking as discussed herein. For example, the processors or computers described in U.S. Pat. No. 6,159,150, filed Nov. 20, 1998, the disclosure of which is incorporated herein by reference, is used.

Accurate motion estimation is provided using one or more of various methods. A first method for providing accurate motion estimation corrects estimates for the motion of the ultrasound transducer 104. A second method of accurate motion estimation determines tissues motion in two dimensions, such as determining a velocity vector.

For the first method, the Doppler processor 120 estimates tissue motion relative to the transducer 104. The transducer 104 may move relative to the tissue region of interest within the patient. For example, intercardiac transducers typically move due to the blood flow and tissue contractions associated with the heart cycle.

FIG. 2A is a graphical representation of the relationship between the transducer 104 and tissue structure 202 within the scan plane 204. As shown in FIG. 2B, the transducer 104 rotates and translates to change the relative position of the tissue structure 202. FIG. 2C represents the apparent movement of the tissue structure 202 due to movement of the transducer 104. By tracking movement of the transducer 104, motion attributable to movement of the tissue structure 202 within the target is isolated from apparent motion due to movement of the transducer 104.

The motion of the transducer 104 is measured using the motion sensor 106. The translation and rotation in one, two or three dimensions is determined by the motion sensor 106 and provided to the controller 116. The controller 116 calculates the magnitude and angle of the motion attributable to motion of the transducer 104.

Alternatively or additionally, ultrasound data, such as B-mode ultrasound data or in-phase and quadrature or radio frequency data from the receive beamformer 108 is used to determine motion of the transducer 104. In one embodiment, a feature likely to be stationary is identified from the ultrasound data. For example, the interventricular septum may be assumed to be stationary. Any apparent motion of the feature reflects motion by the transducer 104. The feature may be identified by applying an algorithm searching for regions of high gradient within the ultrasound data, such as B-mode ultrasound data, shaped like the tissue structure. Alternatively, the user identifies the feature to be tracked. In another embodiment, the speckle associated with the ultrasound data is tracked.

The feature or speckle associated with the ultrasound data is tracked through correlation of ultrasound data. Ultrasound data representing the speckle or feature at different times is correlated. The relative translation and rotation between the ultrasound data associated with the highest correlation or lowest decorrelation indicates the angle and magnitude of movement of the transducer 104. For example, correlation coefficients or the minimum of sum of absolute differences between the two sets of ultrasound data is determined. Such processes are disclosed in U.S. Pat. No. 6,014,473, the disclosure of which is incorporated herein by reference. Various data minimization and correlation simplification algorithms may be used, such as disclosed in the above-referenced patent.

The position of the ultrasound transducer 104 is determined for each frame or scan of data. For example, the difference in the transducer position 104 before and after acquiring a frame of ultrasound data is determined. This difference is divided by the time between the position measurements to determine a rate of movement. Where multiple position measurements are computed during the acquisition of a single frame of ultrasound data, then the scanned region represented by the ultrasound data is divided so that motion estimates for each portion of the scan are corrected as a function of the appropriate position measurements. Alternatively, the transducer motion associated with one or more frames or scans is interpolated or extrapolated from measured transducer motion at other times.

For motion within the scan plane (i.e., assuming no elevation motion), the estimates of motion of the tissue structure 202 or other motion of tissue or fluids is determined as a function of a change or motion along the x-axis, along the y-axis and rotation. Using the center of the transducer array or other location as a reference origin, the rotation θ gives an additional x-axis and y-axis displacement calculated using the matrix below:

$$\begin{bmatrix} \Delta x \\ \Delta y \end{bmatrix} = \begin{bmatrix} \cos\theta & \sin\theta \\ -\sin\theta & \cos\theta \end{bmatrix} \begin{bmatrix} x \\ y \end{bmatrix}$$

The total x-axis and y-axis displacements divided by the time over which the displacement occurs provides spatially varying two-dimensional velocities throughout the scanned region. These velocities are subtracted from Doppler velocity estimates. Preferably, the subtraction accounts for the angle of the motion of the transducer 104 relative to the scanline. For example, the motion of the transducer 104 along the scanline is determined for correcting motion estimated in the direction of the scanline. Where two-dimensional estimates of motion or velocity vectors are used, the motion in two dimensions associated with the transducer 104 is subtracted from the estimated velocity vector.

In alternative embodiments, the transducer motion is determined in three dimensions. Where three dimensional velocity vectors are estimated, the three-dimensional transducer motion is subtracted. For three-dimensional correction, rotation in each of the three dimensions is preferably also determined. In yet other alternative embodiments, transducer motion is determined in only one dimension, such as the direction of scan lines. Rotation may be determined in fewer, none or more dimensions than translation.

Accounting for transducer motion is performed at each of a plurality of locations within the scanned region of the target. In one embodiment, each estimate of motion from the ultrasound data is altered as a function of the motion of the transducer 104. In alternative embodiments, a subset of motion estimates represented by Doppler velocities are corrected as a function of transducer motion.

Figure 3A:
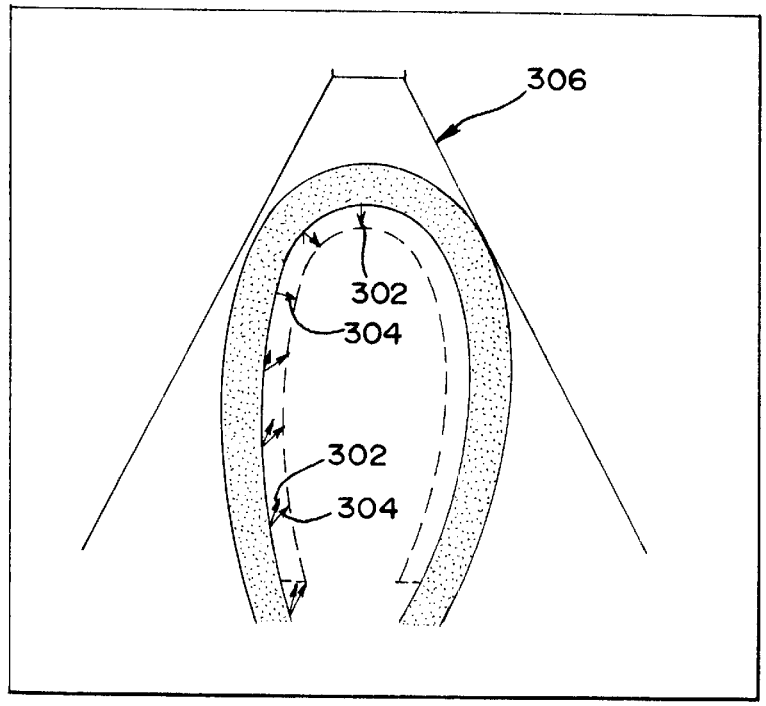
FIGS. 3A and 3B are graphical representations showing tissue motion.
Figure 3B:
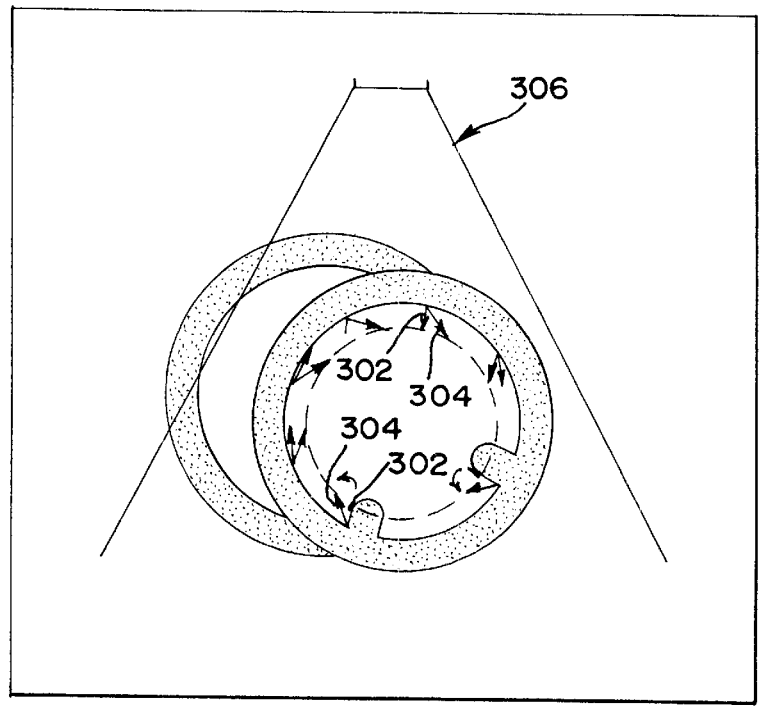

The second method for generating accurate motion estimates comprises determining at least two dimensional velocity vectors or the magnitude of the velocity in a two dimensional plane. FIGS. 3A and 3B show the contraction of the left ventricle from an apical view and a short axis view, respectively. Solid lines represent the left ventricle at a first point in time. The dashed line represents one border of the left ventricle at a different point in time. The velocity vectors 304 represent the magnitude and angle of motion from the first to the second times (the two dimensional velocity). The magnitude of velocity or motion along ultrasound lines within the scans 306 is shown as vectors 302. The vectors 302 represent the magnitude of the motion or velocity of the two-dimensional vectors 304 in one dimension. The velocity along the scanlines represents a velocity determined using Doppler or correlation processing with an ultrasound system. By accounting for an angle of motion, the two-dimensional velocity vector 304 is determined.

The angle of motion or angle of the two-dimensional velocity vector is determined in response to user input or tracking the motion as a function of ultrasound data. For example, speckle or features at one or more locations represented by the ultrasound data are tracked as a function of time.

The relative position of speckle or a feature is tracked between two or more frames or sets of ultrasound data using B-mode ultrasound data. Alternatively, accurate tracking is performed using coherent in-phase and quadrature ultrasound data output by the receive beamformer, so that lateral motion correction may be estimated with an error of less than the ultrasound scan line spacing. In yet other alternative embodiments, other ultrasound data, such as Doppler or motion data, is used for tracking.

Speckle tracking provides an indication of how tissue has moved from one frame of ultrasound data to a subsequent frame of ultrasound data. The speckle pattern is tracked using an iterative search technique. The frames of ultrasound data are compared in various relative positions to find the maximum correlation coefficient or minimum sum of absolute differences. In alternative embodiments, a decorrelation or loss of correlation is calculated. Various techniques may be used for tracking or for simplifying the speckle such as techniques disclosed in U.S. Pat. No. 6,014,473, (Ser. No. 09/196,986, filed Nov. 20, 1998), U.S. Pat. No. 6,352,508, the disclosures of which are in herein by reference in their entirety. For example, the speckle or feature tracking is performed using coarsely spaced samples. Samples associated with higher or the highest values or other prominent structures or features within the tissue are tracked. In alternative embodiments, the tracking information is responsive to user input, such as user input of a border, an angle or a magnitude.

Features represented by the ultrasound data may be tracked. Various contour identifying methods may be used. For example, a user identifies one or more common features or structure in a number of sequential images. As another example, a threshold is applied to identify tissue structures. A border associated with the tissue structures is determined, and the border is tracked from one frame of ultrasound data to another. In another embodiment, gradient or variation in subsets of the ultrasound data of each frame is calculated. Areas of maximum gradient are correlated with areas of maximum gradient in other sets of frames of ultrasound data. Various correlation techniques may be used, such as cross-correlation, decorrelation, minimum sum of absolute differences or other algorithms for comparing the ultrasound data or gradient ultrasound data. Such techniques are described in U.S. Pat. No. 6,159,152, the disclosure of which is incorporated herein by reference.

For imaging moving tissue, a plurality of local regions is tracked. For example, the ventricle shown in FIGS. 3A and 3B shows movement of the ventricle in different directions. By tracking localized regions, the angle and magnitude of motion for a plurality of locations is determined within each set of ultrasound data. In one embodiment, the frame of ultrasound data is divided into nine distinct regions. In alternative embodiments, the motion is tracked for smaller or larger regions.

For each pixel or sample region, an angle, magnitude and/or velocity is determined using the tracking. The speckle or feature tracking provides an angle of motion for each of a plurality of locations. By determining a localized direction of motion, a spatially varying angle correction is applied to the velocity estimates. A magnitude or amount of motion may also be provided. A velocity is determined by dividing the magnitude of the motion by the time between the correlated or tracked frames of data.

Where motion is tracked for a region, the angle, magnitude, and velocity of spatial locations between tracked regions is interpolated. As an alternative to interpolation, the coarsely spaced motion estimates are weighted and averaged where the weighting is a function of the distance between the motion tracking regions. Assume the velocities $V_1, V_2, \ldots V_N$ are measured, (such as by speckle or feature tracking), at points P1, P2, . . . Pn respectively.

The velocity $\hat{V}_k$ at point $P_k$ is estimated by a weighted average of the measured velocities:

$$\hat{V}_k = \frac{\sum_{i=1}^{N} V_i w(d_{ik})}{\sum_{i=1}^{N} w(d_{ik})}$$

where $d_{ik}$ is the distance from $P_i$ to $P_k$ and $w(\cdot)$ is a monotonically decreasing weighting function.

A preferred weighting function is a gaussian function:

$$w(x) = e^{-\pi \left(\frac{x}{\sigma}\right)^2}.$$

In this function, σ is a scaling team and may be set to a value approximately equal to the distance between neighboring measurement points. The value of σ may be appropriately increased if the velocity measurements are noisy. Other weighting functions may be used. Other interpolation or estimation techniques may be used. For example, the angle, magnitude and velocity determined for the nearest location is used.

Motion tracking as described above provides a two-dimensional velocity vector. In alternative embodiments, accurate tissue motion is provided by using an angle determined using the tracking discussed above. The tissue velocity magnitude is determined as a function of Doppler ultrasound data. The Doppler processor 120 identifies the component of the velocity for locations along each ultrasound line. For each sample or pixel location along the ultrasound line, the motion estimate is altered as a function of the angle of motion. The accurate estimate is determined by dividing the magnitude of velocity along the scanline by the cosine of the angle of motion where the angle of motion is relative to the ultrasound beam direction or scanline. In yet other embodiments, the magnitude of velocity determined using just tracking is averaged or combined with the magnitude of velocity determined using the angle and Doppler velocity along the scanlines. Other weighted combinations of the two dimensional velocity estimates may be used.

In other embodiments, different combinations of the two two-dimensional velocity vectors are provided. For example, the two-dimensional velocity magnitude determined using velocity magnitudes along a scanline is used where the angle of motion is more parallel to the ultrasound scanlines. The two-dimensional velocity magnitude determined using the tracking is used where the angle of motion is close to 90° (e.g., between 75° and 105°) to the ultrasound scanlines. In this case, since the estimate of velocity or motion provided by the Doppler processor 120 is based on a calculation of velocity along the scanlines, more accurate velocity estimates are provided using the magnitude of velocity determined from the tracking.

In one embodiment, the tracking information is used to improve the velocity estimated using other techniques, such as to correct for velocity estimate aliasing. The two-dimensional velocity magnitude and angle estimated using a tracking method discussed above is used to calculate the velocity or magnitude of motion along the scanlines. The tracking velocity along the scanline is compared to the Doppler velocity determined along the scanline. If the two values are substantially different, aliasing is likely. An indication maybe provided to the user. The system may automatically increase the velocity range. Additionally or alternatively, a new velocity value is calculated from the Doppler velocity estimate and the tracking velocity estimate. The magnitude of the new velocity value is equal to the Doppler velocity estimate plus an integer n times the Nyquist velocity range, where this sum is divided by the cosine of the direction of motion relative to the ultrasound line. The integer n is selected such that the new velocity estimate and the tracking velocity are minimized. Mathematically, let $D_v$ be the Doppler velocity estimate, $N_v$ be the Nyquist velocity range, $T_v$ be the tracking velocity, and $\theta$ be the tracking velocity angle relative to the scan line. The magnitude of the new velocity is given by $$v_{new} = \frac{D_v + n*N_v}{\cos(\theta)}$$

The integer n is the integer that minimizes $|v_{new}-T_v|$. The integer n may be negative, zero, or positive. The direction of the new velocity is equal to the direction of motion determined by tracking.

With this technique, the velocity scale may be lowered for greater precision and better estimates from the Doppler processor 120. As discussed below, the unaliased velocity estimates may be used for calculating strain rates.

In another embodiment, a three-dimensional velocity magnitude is calculated for further accuracy. A two-dimensional velocity vector is calculated as discussed above. A magnitude of the velocity in the elevation or third dimension is computed as a function of a loss of correlation measurement. A relationship of the loss of correlation of speckle to the magnitude of motion is determined experimentally. For example, fully developed speckle is assumed, and decorrelation is measured as a function of controlled motion while imaging a phantom at a number of depths. The rate of decorrelation as a function of the elevation beam width, a known factor, and distance from the transducer provide further variables. During use of the system 100 and based on these variables and a measured loss of correlation, a magnitude of motion or velocity in the third or elevation dimension is determined. The loss of correlation is calculated for the plurality of localized regions. Preferably, loss of correlation is calculated for regions associated with the highest in-plane correlation. The two dimensional velocity is combined with the orthogonal or velocity estimate in the third dimension using Pythagorean's theorem. The three dimensional velocity is equal to the square toot of the two-dimensional velocity squared plus the velocity in the third dimension squared. In alternative embodiments, the user inputs one or more velocities for motion in the elevation dimension. These velocities may be based on imaging the tissue from another angle. In the case of cardiac motion, care is taken to use velocities from an appropriate or similar time in the cardiac cycle.

Using one or more of the techniques described above, accurate velocity estimates as a function of the magnitude of velocity, the direction of the velocity or a combination thereof is used for generating a tissue motion image. The tissue motion image may be overlaid with a B-mode image. A sequence of images representing the tissue as a function of time may be generated. In one embodiment, a two-dimensional image representing a region is generated from the accurate velocities on the display alone or in combination with other images. In alternative embodiments, three-dimensional images are generated. In yet other alternative embodiments, one-dimensional images are generated, such as images showing velocities along a line as a function of time or velocities at a point or region as a function of time.

The accurate velocity angle or magnitude information is used for further quantification or calculations. In one embodiment, a characteristic of strain is measured from the velocities estimated as discussed above. For example, the strain rate or strain is determined. Strain rate is the spatial derivative of the tissue velocity. Tissue velocity is a temporal derivative of the tissue position. The spatial derivative is calculated along each of the dimensions for which velocity magnitude is known. For example, the strain rate along the x direction, y direction and z direction is determined. Further, the shear strain rates may be calculated, such as calculating the derivative in one direction of a velocity in a different direction.

Other coordinate systems may be used. For example, a cylindrical coordinate system may be used for describing left ventricular motion. The ventricular motion is then provided in terms of longitudinal, rotational and radial motion.

Where a two-dimensional velocity vector is available, the spatial derivative is determined along the direction of a maximum velocity or along an axis parallel to the angle of motion. Alternatively, the strain rate is independently computed for each of the two dimensions and combined. With a two-dimensional velocity estimate, three of the six possible components of strain rate are determined. Alternatively, the strain rate is determined in the direction of local motion.

To determine the strain rate in a region, velocities at two points separated by a certain distance are selected. For example, the distance is a centimeter relative to the target being imaged. Other distances, including lesser or greater distances may be used. The velocities at these two points are subtracted, and the difference is divided by the distance between the two points. For better spatial resolution with worse precision, the distance between the two selected points is smaller. Conversely, a larger distance is used to provide better precision with less spatial resolution. Using two-dimensional velocities, three-dimensional velocities, or velocities altered as a function of transducer motion or angle of motion, an accurate strain rate is provided.

The strain rate can be calculated for a plurality of tissue regions. For example, the strain rate along a continuum or line of interest is calculated. The calculated strain rates are low pass filtered or otherwise processed. In alternative embodiments, no further processing is provided. Likewise, the velocity estimates, regardless of the estimation technique, may be low pass filtered or otherwise processed prior to calculating the strain rate. Characteristics of the strain rate may also be calculated, such as the maximum or average strain rate during one or more cardiac cycles, or portions thereof.

To provide more accurate diagnosis, calculations such as strain rate, are performed as a function of time for the same tissue. Rather than performing a calculation for data positioned relative to the transducer 104, the ultrasound data for the calculations is selected as a function of the tracking discussed above. For example, a tissue or tissue region associated with a calculation is tracked as a function of time from one frame of ultrasound data to another frame of ultrasound data. The ultrasound data used for performing the calculation relating to that tissue region is selected as a function of the position of the tissue. The tissue within a two or three-dimensional region is tracked. Alternatively, the position along a line is tracked (e.g. M-mode imaging). The calculation, such as strain rate, provides information specific to that tissue rather than information specific to the same location relative to the transducer 104.

Another calculation benefiting from accurate velocity estimates is strain. Strain is the time integral of the strain rate. In one embodiment, the strain is calculated for one or more regions. Preferably, the strain rate and associated strain values are calculated for the same tissue as that tissue moves relative to the transducer 104 as discussed above. Any of various ranges of time may be used for determining the strain. For example, an ECG signal or variance in Doppler information is used to identify an R-wave of the heart cycle. The strain is computed for data acquired beginning at the R-wave of the heart cycle through at least one subsequent cardiac cycle. Averages of the strain over multiple cardiac cycles may be obtained. As another example, the ultrasound data or another measuring device is used to determine the closing of the mitrial valve. The strain is calculated from the closing until a subsequent closing of the mitrial value.

Where calculations are performed as a function of time, such as strain, the ultrasound data used may include additional data for temporal resolution. For example, data from a plurality of heart cycles is combined to represent data over one heart cycle. In one embodiment, frames of ultrasound data are acquired at set points relative to an ECG or the heart cycle in response to triggering. For subsequent heart cycles, an off-set is applied to the set points. When combined, a greater number of instances within a heart cycle relative to the heart cycle are represented by ultrasound data. In another embodiment, ultrasound data from multiple cycles without triggering are acquired. Using a tracked time of acquisition for the frame or portion of the frame and relative heart cycle position, the frames of ultrasound data are combined for better temporal resolution. Additionally, considering the precise time when each portion of an image is acquired will improve the temporal precision of a strain rate or a strain rate derived measurement.

A characteristic of strain or other calculated values is displayed or stored. Various displays may be used, such as displaying the values as a function of time. For example, a quantity is displayed. As another example, a graph representing that value as a function of time is displayed. Further quantifications may be performed, such as calculating the peak strain rate or strain.

In one preferred embodiment, two-dimensional velocity information is calculated as discussed above. The two-dimensional velocity information is altered to account for transducer motion relative to the region of interest. The altered two-dimensional velocity information is used for displaying an image and/or to calculate strain rate and strain values.

While the invention has been described above by reference to various embodiments, it will be understood that many changes and modifications can be made without departing from the scope of the invention. For example, different processors and systems may be used for performing any of the various calculations discussed herein. Velocity information may be calculated from time shift information, Doppler processing, or autocorrelation processing. Additional corrections or alterations of the velocity values, such as filtering or accounting for other factors, may be provided.

It is therefore intended that the foregoing detailed description be understood as an illustration of the presently preferred embodiments of the invention, and not as a definition of the invention. It is only the following claims, including all equivalents that are intended to define the scope of this invention.

What is claimed is:

1. A method for providing motion estimates of a target with an ultrasound system, the method comprising the acts of:
   (a) determining with a motion processor a first motion angle from ultrasound data as a function of speckle or a feature;
   (b) estimating a first velocity magnitude with the motion processor as a function of ultrasound data; and
   (c) determining a second velocity magnitude responsive to the motion angle and the first velocity magnitude.

2. The method of claim 1 further comprising:
   (d) measuring motion of a transducer array with an electromagnetic position sensor; and
   (e) altering one of the first and second velocity magnitudes as a function of the measured motion of (d).

3. The method of claim 1 wherein (a) comprises determining the first motion angle as a function of speckle represented by the ultrasound data.

4. The method of claim 1 wherein (a) comprises determining the first motion angle as a function of the feature of the target represented by the ultrasound data.

5. The method of claim 1 wherein the target comprises tissue and (a) comprises determining the first motion angle of the tissue.

6. The method of claim 1 further comprising:
   (d) determining a second motion angle corresponding to motion along an elevation axis;
       wherein (c) comprises determining the second velocity magnitude as a function of the second motion angle, the first motion angle and the first velocity magnitude.

7. The method of claim 1 further comprising:
   (d) estimating a third velocity magnitude as a function of the speckle or feature; and
   (e) comparing the first motion angle to a close to orthogonal threshold;
       wherein (c) comprises determining the second velocity magnitude as a function of the third velocity magnitude in response to (e).

8. The method of claim 1 wherein (c) comprises dividing the first velocity magnitude by a cosine of the first motion angle.

9. The method of claim 1 wherein (a) comprises determining the first motion angle as a function of the speckle or feature represented by coherent ultrasound data.

10. The method of claim 1 further comprising:
    (d) calculating a characteristic of strain as a function of the second velocity magnitude.

11. The method of claim 1 further comprising:
    (d) performing (a), (b) and (c) for each of a plurality of local regions within a scanned region of the target.

12. A method for providing motion estimates of a target tissue with an ultrasound system, the method comprising the acts of:
    (a) determining with a processor at least first and second motion angles for at least first and second local regions, respectively, as a function of ultrasound data, the first local region a different region than the second local region; and
    (b) adjusting at least first and second tissue motion estimates for the at least first and second local regions, respectively, as a function of the at least first and second motion angles, respectively.

13. The method of claim 12 further comprising:
    (c) determining a characteristic of tissue strain as a function of the at least first and second tissue motion estimates.

14. A method for providing motion estimates of a target with an ultrasound system, the method comprising the acts of:
    (a) measuring a velocity vector representing at least two-dimensions as a function of ultrasound data; and (b) calculating a characteristic of strain as a function of the velocity vector.

15. The method of claim 14 wherein (a) comprises determining the velocity vector as a function of speckle or a feature of the target represented by the ultrasound data.

16. The method of claim 14 wherein (a) comprises measuring a velocity vector representing three-dimensions.

17. The method of claim 14 wherein (b) comprises calculating a maximum velocity strain.

18. The method of claim 14 further comprising:
(c) performing (a) for a plurality of locations;
  wherein (b) comprises calculating the characteristic of strain as a function of the velocity vector for at least two of the plurality of locations.

19. The method of claim 18 further comprising:
(d) adjusting a Doppler velocity estimate as a function of a tracking velocity estimate.

20. The method of claim 18 further comprising:
(d) tracking the at least two of the plurality of locations as a function of time;
  wherein (b) comprises calculating strain as a function of the velocity vector for the at least two of the plurality of locations as a function of time with ultrasound data selected as a function of (d).

21. The method of claim 18 further comprising:
(c) determining a time in a heart cycle; and
(d) calculating strain as a function of (c) and (b) where the characteristic of strain comprises a strain rate.

22. A medical diagnostic ultrasound system for providing motion estimates of a target, the system comprising:
  a motion processor for measuring a velocity vector representing at least two-dimensions as a function of ultrasound data; and
  a strain processor for calculating a characteristic of strain as a function of the velocity vector.

* * * * *